United States Patent [19]

Dijk et al.

[11] Patent Number: 4,851,451

[45] Date of Patent: Jul. 25, 1989

[54] CATALYST COMPOSITIONS AND A PROCESS FOR THE PREPARATION THEREWITH OF HYDROCARBONS FROM SYNTHESIS GAS

[75] Inventors: Arjan V. Dijk; Swan T. Sie, both of Amsterdam, Netherlands

[73] Assignee: Shell Oil Company, Houston, Tex.

[21] Appl. No.: 224,635

[22] Filed: Jul. 27, 1988

Related U.S. Application Data

[62] Division of Ser. No. 65,752, Jun. 24, 1987, abandoned.

[30] Foreign Application Priority Data

Jul. 2, 1986 [GB] United Kingdom ............... 8616161

[51] Int. Cl.$^4$ ................................................. C07L 1/06
[52] U.S. Cl. ................................ 518/714; 502/250; 502/73
[58] Field of Search ........................................ 518/714

[56] References Cited

U.S. PATENT DOCUMENTS

| | | | |
|---|---|---|---|
| 4,180,516 | 12/1979 | Chang et al. ................ | 260/449 |
| 4,259,306 | 3/1981 | Pelrine ........................... | 423/325 |
| 4,390,457 | 6/1983 | Klotz .............................. | 252/455 |
| 4,495,166 | 1/1985 | Calvert et al. ................ | 423/329 |
| 4,578,259 | 3/1986 | Morimoto et al. .......... | 423/329 |
| 4,613,488 | 9/1986 | Van Erp et al. ............. | 423/328 |

FOREIGN PATENT DOCUMENTS

| | | |
|---|---|---|
| 2053960 | 2/1981 | United Kingdom . |
| 2122637 | 1/1984 | United Kingdom . |
| 2144727 | 3/1985 | United Kingdom . |

OTHER PUBLICATIONS

B. M. Lok et al., "The Role of Organic Molecules in Molecular Sieve Synthesis", Zeolites, 1983, vol. 3, Oct., pp. 282-291.

*Primary Examiner*—Howard T. Mars
*Attorney, Agent, or Firm*—Kimbley L. Muller

[57] ABSTRACT

A catalyst composition which contains at least one metal from Group 2b and at least one metal from Group 6b of the Periodic Table of the Elements or compounds thereof and a crystalline aluminum silicate which is obtained by crystallizing an aqueous alkaline starting mixture comprising at least one silicon compound, at least one aluminum compound, at least one compound of a metal from Group 1a of the Periodic Table of the Elements (MX) and organic nitrogen compounds at an elevated temperature until said crystalline aluminum silicate is formed and subsequently separating crystalline aluminum silicate from the mother liquor, in which starting mixture the compounds are present in the following molar ratios:

RN: $R_4NY = 1-1000$,
$SiO_2$: $R_4NY = 10-5000$,
$SiO_2$: $Al_2O_3 = 50-300$,
$SiO_2$: $MX < 15$, and
$H_2O$: $SiO_2 = 5-100$, where RN represents a pyridine and $R_4NY$ represents an organic quaternary ammonium compound. The catalyst composition can be used in a process for the preparation of hydrocarbons from synthesis gas.

3 Claims, No Drawings

CATALYST COMPOSITIONS AND A PROCESS FOR THE PREPARATION THEREWITH OF HYDROCARBONS FROM SYNTHESIS GAS

This is a division, of application Ser. No. 065,752, filed June 24, 1987 and now abandoned.

The invention relates to a catalyst composition which is suitable for use in a process for the preparation of hydrocarbons from synthesis gas.

Catalyst compositions containing zinc and chromium as metals from Groups 2b and 6b, respectively, of the Periodic Table of the Elements in combination with a crystalline aluminum silicate are known to possess catalytic activity for the conversion of synthesis gas into hydrocarbons.

However, a disadvantage associated with the use of said catalyst compositions is the relatively high durene production observed during the preparation of hydrocarbons therewith. In view of the relatively high melting point of durene, the presence thereof in considerable quantities in synthesized hydrocarbons which are to be further processed, or applied as gasoline, is highly undesirable. Moreover, the stability of the aforementioned catalyst compositions is in some cases lower than would be desirable for the application thereof on a commercial scale.

In U.S. Pat. No. 4,180,516, issued to Chang et al, a synthesis gas is converted to aromatic hydrocarbons in the presence of a $ZnO-Cr_2O_3$ mixed catalyst having an atomic ratio of Zn to Cr of less than about 4.1. A second component is a selected crystalline aluminosilicate having a silica alumina ratio of greater than 12:1 and a pore size of 5 Å. The latter component is exemplified by ZSM-5, ZSM-11, ZSM-12, ZSM-35 and ZSM-38, none of which is believed to employ a template director comprising both a pyridine and an organic quaternary ammonium compound.

Surprisingly, it has now been found that catalyst compositions having excellent properties for use in various processes can be reproduceably prepared from particular crystalline aluminum silicates, provided that the various compounds required for synthesizing said silicates are present in the starting mixture in specific molar ratio ranges.

The invention therefore relates to a catalyst composition which contains at least one metal from Group 2b and at least one metal from Group 6b of the Periodic Table of the Elements or compounds thereof and a crystalline aluminum silicate which is obtainable by maintaining an aqueous alkali starting mixture comprising at least one silicon compound, at least one aluminum compound, at least one compound of a metal from Group 1a of the Periodic Table of the Elements (MX) and organic nitrogen compounds at an elevated temperature until crystalline aluminum silicate has formed and subsequently separating crystalline aluminum silicate and the mother liquor, in which starting mixture the various compounds are present within the following molar ratios:

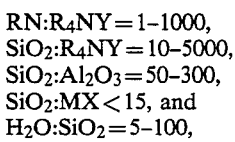

$RN:R_4NY = 1-1000$,
$SiO_2:R_4NY = 10-5000$,
$SiO_2:Al_2O_3 = 50-300$,
$SiO_2:MX < 15$, and
$H_2O:SiO_2 = 5-100$, where RN represents a pyridine and $R_4NY$ represents an organic quaternary ammonium compound.

The Periodic Table of the Elements referred to is stated in the "Handbook of Chemistry and Physics", 55th edition, CRC Press, Ohio, USA (1975).

RN is chosen from a compound selected from the group consisting of pyridine, alkyl pyridines and (substituted alkyl) pyridines, wherein the alkyl-groups preferably comprise from 1–4 carbon atoms, and amino pyridines; most preferably RN represents pyridine.

The R groups in $R_4NY$ suitably comprise four of the same or different alkyl-groups and/or substituted alkyl-groups, e.g. alkyl-groups comprising a hydroxy- and/or a halogen (e.g. bromine)substituent; these alkyl-groups generally comprise from 1–20, preferably from 1–4 carbon atoms. The symbol Y in $R_4NY$ suitably represents an anion of a mineral acid or a hydroxyl ion. Preferably $R_4NY$ represents tetrapropyl ammonium hydroxide, a suitable alternative therefore being tetraethyl ammonium bromide.

The above-defined organic nitrogen compounds RN and $R_4NY$ are preferably present in the starting mixture in a molar ratio from 5–200, and most preferably from 10–75, which means that the molar quantity of compound $R_4NY$ is preferably substantially smaller than the employed molar quantity of compound RN. The molar ratio in which $SiO_2$ and $R_4NY$ are present in the starting mixture is preferably from 20–400, and most preferably from 30–300.

The compound MX in the starting mixture preferably represents at least one of $M_nZ$ and at least one of MOH in which M represents an alkali metal ion and Z represents an anion of a mineral acid (n satisfying the electroneutrality of the compound $M_nZ$); most preferably M represents a sodium ion. The compounds $SiO_2$ and MOH are suitably present in the starting mixture in a molar ratio of from 5.2–7.8, preferably of from 5.6–7.0. In any case the aqueous starting mixture has an alkali character which means that the pH of the starting mixture is greater than 7.

The compounds $SiO_2$, $Al_2O_3$ and $H_2O$ are preferably present in the starting mixture in the following molar ratios: $SiO_2:Al_2O_3 = 65-200$, and $H_2O:SiO_2 - 8-60$.

In the starting mixture used in the preparation of a crystalline aluminum silicate for a catalyst composition according to the present invention various silicon- and aluminum compounds may be present. Suitable silicon compounds include water glass and amorphous silica, while suitable aluminum compounds include aluminum sulphate and sodium sulphates, nitrates and phosphates. It is not necessary, however, that the above-mentioned compounds are added to the aqueous starting mixture in that form. They may also be formed from other reaction components, for instance from water glass and sulphuric acid. A very suitable starting mixture comprises amorphous silica, aluminum sulphate, sodium hydroxide, sodium sulphate, pyridine, water and either tetrapropyl ammonium hydroxide or tetraethyl ammonium bromide.

The crystalline aluminum silicates are suitably prepared in the manner as described hereinbefore by maintaining the starting mixture, usually under autogenous pressure, at an elevated temperature, preferably from 100°–250° C. for 24–190 hours, preferably from 30–120 hours, under stirred conditions, until the appropriate crystalline aluminum silicate has formed and subsequently separating crystalline aluminum silicate from the motor liquor (e.g. by means of filtration or centrifugation), washing the crystalline aluminum silicate thus obtained and drying (suitably at a temperature of from 100°-200° C.), optionally followed by calcining at a temperature of from 200°-600° C.

The present invention relates in particular to a catalyst composition which contains at least one metal from Group 2b and at least one metal from Group 6b of the Periodic Table of the Elements or compounds thereof and a crystalline aluminum silicate having a characteristic X-ray diffraction pattern substantially as shown in Table A and discussed hereinafter.

The crystalline aluminum silicates as synthesized contain alkali metal. An alkali metal content of more than 0.1% by weight is undesirable, however, when catalyst compositions containing the crystalline aluminum silicates are to be used in a process for the preparation of hydrocarbons by contacting synthesis gas at hydrocarbon synthesis conditions with said catalyst composition, to which process the present invention also relates. In order to reduce the alkali metal content of the silicates to less than 0.1% by weight and in particular to less than 0.01% by weight, the silicates are suitably contacted once or several times with an aqueous solution which comprises ammonium ions. From the $NH_4^+$ aluminum silicates obtained in this manner the $H^+$ aluminum silicates can be prepared by calcination.

The catalyst composition according to the invention preferably contains zinc together with chromium as metals from Groups 2b and 6b, respectively, in particular in the form of their oxides ZnO and $Cr_2O_3$. The weight ratio of zinc and chromium (calculated on the basis of the sum of said oxides) to crystalline aluminum silicate is preferably from 0.1-10, and in particular from 0.2-7. The molar percentage of zinc, based on the sum of zinc and chromium is preferably from 50-95%, and in particular from 60-80%.

The catalyst composition according to the invention may be a macro- or a micro-mixture. In the first case the composition comprises two kinds of micro-particles, of which one kind consists of Groups 2b and 6b metals or compounds thereof and the other kind consists of crystalline aluminum silicate. In the second case, the composition comprises one kind of macroparticles, each macroparticle being built up from a substantial number of microparticles of each of said metals (or compounds thereof) and of the aluminum silicate. Catalyst compositions in the form of micromixtures may be prepared e.g. by thoroughly mixing a fine powder of oxides of the metals in question with a fine powder of the aluminum silicate and shaping the resulting mixture into larger particles (preferably having a diameter from 0.2-5 mm) e.g. by extruding or tabletting. Catalyst compositions in the form of physical micromixtures are preferred for use in the hydrocarbon synthesis process according to the present invention.

During shaping the catalyst compositions may be combined with a binder material, suitably in a weight ratio from 1-10 catalyst to binder; preferably a binder material such as alumina is used which contains no or only very little alkali metal. The binder material may also exert catalytic activity if so desired. Catalytically active metals can be suitably deposited on the binder material (e.g. by means of ion exchange) before combining it with the afore-described catalyt composition. However, it is also possible to impregnate an extrudate of the catalyst composition and a binder material with a metal (compound) in order to prepare catalysts.

It has further more been found that the catalyst compositions according to the present invention can be improved (in particular with respect to their stability and to a further decrease in durene formation in a hydrocarbon synthesis process) by using them simultaneously as carrier for at least one additional metal from Groups 1a, 2a, 4b, 7b and 8 of the Periodic Table of the Elements or a compound thereof. Preferred metals are calcium, magnesium, titanium, zinc and in particularly manganese because it appears that the presence thereof in the catalyst composition leads to a shift in product distribution towards lower boiling aromatic compounds and simultaneously to a reduction of the undesired formation of durene in a hydrocarbon synthesis process to such an extent that further upgrading of the hydrocarbons-containing product is no longer necessary, in particular when the gasoline fraction of said product is to be used as motor fuel. The metals or their components may be deposited on the catalyst compositions by means of any process for the preparation of catalysts known in the art, such as impregnation, ion-exchange or precipitation. It is preferred to incorporate said additional metal(s) by means of impregnation with an aqueous solution of a salt (e.g. the nitrate) thereof followed by drying and calcining of the metal-loaded catalyst composition.

The metal-loaded catalyst compositions preferably contain from 0.1-10% by weight, in particular from 1-5% by weight, of manganese, calculated on the basis of the catalyst composition without manganese.

The process for the preparation of hydrocarbons starts from synthesis gas containing as major components hydrogen and carbon monoxide; in addition the synthesis gas feed may contain carbon dioxide, water, nitrogen, argon and minor amounts of compounds having 1-4 carbon atoms per molecule such as methane, methanol or ethene.

The synthesis gas feed can be prepared in any manner known in the art e.g. by means of steam gasification of a hydrocarbonaceous material such as brown coil, anthracite, coke, crude mineral oil and fractions thereof, and oil recovered from tar sand and bituminous shale. Alternatively, steam methane reforming and/or catalytic partial oxidation of a hydrocarbonaceous material with an oxygen-containing gas can be applied to produce synthesis gas suitable for use in the hydrocarbon synthesis process according to the invention.

A process for the preparation of hydrocarbons from synthesis gas with the catalyst composition according to the present invention is preferably carried out at a temperature from 200°-500° C., a total pressure from 1-200 bar abs., a space velocity from 200-3000 1 (S.T.P.) synthesis gas/kg catalyst/hour and a $H_2/CO$ molar feed ratio from 0.3-5. Preferably preferred process conditions include a temperature from 300°-450° C., a pressure from 5-100 bar abs., a space velocity from 400-2000 1 (S.T.P.) synthesis gas/kg catalyst/hour and a $H_2/CO$ molar feed ratio from 0.4-2. The expression "S.T.P." as referred to hereinbefore means Standard Temperature (of 0° C.) and Pressure (1 bar abs.).

Furthermore, the present invention relates to hydrocarbon-containing mixtures (suitably containing aromatic-, naphthenic- and/or acyclic-compounds which may further contain oxygen and/or light olefins) whenever prepared according to a process as described hereinbefore.

EXAMPLE 1

(a) Preparation of crystalline aluminum silicates A and B.

An aqueous alkaline starting mixture was prepared by adding to water the following compounds: amorphous silica, aluminum sulphate, sodium sulphate, sodium hydroxide, pyridine and tetrapropyl ammonium hydroxide in such quantities that the starting mixture had the following molar composition: $93.5SiO_2$-$1Al_2O_3$-$30C_5H_5N$-$0.5(C_3H_7)_4NOH$-$7Na_2O$-$19.6Na_2SO_4$-$1938H_2O$.

Aluminum silicate A was prepared by maintaining the starting mixture at 150° C. for 72 hours with stirring in an autoclave under autogenous pressure. After cooling, the reaction mixture crystalline aluminum silicate was filtered off, washed with water until the pH of the wash water was about 8 and dried at 120° C. for 16 hours; the dried crystalline aluminum silicate was calcined in air at 538° C. for two hours followed by an ammonium-exchange treatment and subsequently calcining in air at 500° C. for one hour to obtain the aluminum silicate in the $H^+$ form. The so obtained aluminum silicate A had the characteristic X-ray diffraction pattern given in Table A, in which "D-space" represents the interplanar spacing (in A) calculated from the measured theta (Bragg angle) by using the Bragg equation and "$I/I_{max}$,%" represents the intensity of a peak, expressed as a percentage of the intensity of the main peak.

TABLE A

| D-space | $I/I_{max}$, % |
|---|---|
| 11.04 | 57 |
| 9.96 | 30 |
| 9.93 | 31 |
| 3.84 | 100 |
| 3.81 | 68 |
| 3.74 | 33 |
| 3.71 | 59 |
| 3.43 | 12 |
| 3.39 | 9 |
| 3.34 | 11 |
| 3.12 | 82 |
| 1.92 | 51 |

Chemical analysis of crystalline aluminum silicate A showed that its aluminum content was 1.2% by weight.

Aluminum silicate B was prepared by using a similar starting mixture as used for aluminum silicate A, except that the molar amount of $(C_3H_7)_4NOH$ was increased from 0.5 to 1.0. The starting mixture was maintained at 150° C. for 72 hours with stirring in an autoclave under autogenous pressure and treated further as described hereinabove for the preparation of aluminum silicate A.

The aluminum silicate B thus obtained gave a similar characteristic X-ray diffraction pattern as shown in Table A.

The aluminum content of aluminum silicate B was 1.2% by weight.

(b) Preparation of catalyst compositions 1 and 2.

From crystalline aluminum silicates A and B catalyst compositions 1 and 2, respectively, were prepared by mixing a combination of ZnO and $Cr_2O_3$ having a Zn:Cr atomic ratio of 66:34 with the respective crystalline aluminum silicates in a weight ratio of 5:1 (calculated on the basis of said zinc- and chromium-oxides).

(c) Preparation of catalyst compositions 3 and 4 containing manganese.

18 Grams each of catalyst compositions 1 and 2 were impregnated with 10 ml of a solution containing 0.93 mol manganese nitrate/1 at a temperature of 25° C., dried at a temperature of 120° C. for 2 hours and then calcined at a temperature of 450° C. for 1 hour. The resulting catalyst compositions 3 and 4, respectively, both contained 2.8% by weight of manganese, calculated on the basis of the catalyst compositions without manganese.

EXAMPLE 2

(a) Preparation of crystalline aluminum silicate C.

Aluminum silicate C was prepared using a similar starting mixture as used for aluminum silicate A, except tht the molar amount of $(C_3H_7)_4NOH$ was decreased from 0.5 to 0.28. The starting mixture was maintained at 150° C. for 75 hours with stirring in an autoclave under autogenous pressure and treated further as described hereinbefore for the preparation of aluminum silicates A and B.

The aluminum silicate C thus obtained showed an X-ray diffraction pattern as given in the following Table B.

TABLE B

| D-space | I/I max, % |
|---|---|
| 11.22 | 41 |
| 10.09 | 22 |
| 9.79 | 11 |
| 3.98 | 13 |
| 3.86 | 100 |
| 3.83 | 71 |
| 3.75 | 44 |
| 3.73 | 56 |
| 3.65 | 37 |
| 3.54 | 15 |
| 3.43 | 22 |
| 3.36 | 11 |
| 3.31 | 19 |
| 3.05 | 13 |
| 2.99 | 14 |
| 2.98 | 15 |

Chemical analysis of composite crystalline aluminum silicate C showed that its aluminum content was 2.7% by weight. Composite aluminum silicate C comprises a crystalline material containing two different crystalline aluminum silicates including a major amount of aluminium silicate A.

(b) Preparation of catalyst composition 5.

From composite aluminum silicate C catalyst composition 5 was prepared in a similar manner as described for catalyst compositions 1 and 2 in Example 1b).

(c) Catalyst composition 6 which contained 2.8% by weight of manganese, calculated on the basis of catalyst composition 5, was prepared from the latter composition in a similar manner as described hereinbefore in Example 1c for catalyst compositions 3 and 4.

COMPARATIVE EXAMPLE (a) Crystalline aluminum silicate D was prepared in a similar manner as aluminum silicate A by using an aqueous alkaline starting mixture having the following molar composition: $93.5SiO_2$-$1.25Al_2O_3$-$33.6(C_3H_7)_4NOH$-$1.25Na_2O$-$1938H_2O$. The characteristic X-ray diffraction pattern of crystalline aluminum silicate D is given in the following Table C.

TABLE C

| D-space | $I/I_{max}$, % |
|---|---|
| 11.03 | 74 |
| 9.90 | 40 |
| 3.84 | 100 |
| 3.80 | 70 |
| 3.73 | 40 |
| 3.70 | 62 |
| 3.42 | 10 |

TABLE C-continued

| D-space | $I/I_{max}$, % |
|---|---|
| 3.39 | 4 |
| 3.34 | 8 |
| 3.13 | 75 |
| 1.92 | 48 |

Aluminum silicate D, which is not a compound of a catalyst composition in accordance with the present invention, comprised a crystalline aluminum silicate with a similar chemical composition as aluminum silicate A. However, by comparing the characteristic X-ray diffraction patters as shown in Tables A and C it will be clear that aluminum silicate D is different from aluminum silicate A or C.

(b) Catalyst composition 7 was prepared from aluminum silicate D in a similar manner as described in Example (1b) for catalyst compositins 1 and 2.

EXAMPLE 3

Hydrocarbon synthesis experiments.

Synthesis gas containing hydrogen and carbon monoxide in a molar ratio of 0.5 was passed with a space velocity of 850 l (S.T.P.)/kg catalyst/hour through a microflow reactor containing catalyst compositions 1, 2, 5 and 7, respectively, with a particle size of 0.2–0.6 mm at a temperature of 375° C. and a pressure of 60 bar abs. The normally liquid product thus obtained contained 4.0% by weight of durene when catalyst composition 1 or 2 was employed whereas with composition 5 a durene-content of only 1.5%w was attained. The liquid product obtained with comparative catalyst composition 7 contained 9.6%w durene, thus showing a shift in product distribution to undesirably high boiling aromatic compounds compared to catalyst compositions 1 and 2.

Further hydrocarbon synthesis experiments were carried out under similar conditions as described hereinbefore using manganese-containing catalyst compositions 3, 4 and 6 and equivalent catalyst compositions 1, 2 and 5, respectively, which did not contain manganese. The results of said experiments are given in the following Table D.

TABLE D

| Catalyst composition | 1 or 2 | 3 or 4 | 5 | 6 |
|---|---|---|---|---|
| durene, % w on aromatics | 9.8 | 6.2 | 7.9 | 5.2 |
| life time, h | 220 | 550 | 100 | 340 |

The expression "life time" as used hereinbefore represents the period (in hours) in which the initial conversion of CO and H$_2$ feed (in % by volume) has been divided by ½. The expression "durene, %w on aromatics" represents the weight percentage of durene based on the amount of aromatic compounds present in the normally liquid product fraction.

From the results given in Table D it will be clear that the incorporation of a relatively small amount (2.8% by weight) of manganese into the catalyst compositions according to the invention leads to a substantial increase in the life time of said compositions, while the formation of durene is even further suppressed.

What we claim as our invention is:

1. A process for the preparation of hydrocarbons from synthesis gas comprising hydrogen and carbon monoxide, with a reduction in the production of durene which comprises contacting said synthesis gas, at hydrocarbon synthesis conditions, with a catalyst composition comprising: at least one metal or compound of metal from Group 2b and at least one metal or compound of metal from Group 6b of the Periodic Table of Elements and a crystalline aluminum silicate crystallized from an aqueous alkaline crystallization mixture comprising at least one silicon compound comprising SiO$_2$, at least one aluminum compound comprising Al$_2$O$_3$, at least one compound of a metal selected from Group 1a (MX) of the Periodic Table of Elements, wherein MX represents at least one M$_n$Z and at least one MOH in which M represents an alkali metal ion, Z represents an anion of a mineral acid and n satisfies the electroneutrality of the compound M$_n$Z and organic nitrogen compounds comprising pyridine or a compound of pyridine represented by the formula (RN) wherein RN is selected from the group consisting of pyridine, alkyl pyridine, alkyl substituted pyridines and amino pyridines and wherein said alkyl groups comprise from one to four carbon atoms and an organic quaternary ammonium compound represented by the formula R$_4$NY wherein in R$_4$NY the R groups comprise four of the same or different groups having from one to twenty carbon atoms selected from alkyl groups, substituted alkyl groups or combinations thereof, wherein the substituents on the alkyl groups are hydroxy and/or halogen, and Y represents an anion of a mineral acid or a hydroxyl ion, in the following mole ratios:

RN:R$_4$NY = 1–1000
SiO$_2$:R$_4$NY = 10–5000
SiO$_2$:Al$_2$O$_3$ = 50–300
SiO$_2$:MX < 15 and
H$_2$O:SiO$_2$ = 5–100.

2. The process according to claim 1 wherein said hydrocarbon synthesis conditions include a temperature from 200°–500° C., a total pressure from 1–200 bars abs., a space velocity from 200–3000 l (S.T.P.) synthesis gas/kg catalyst/hour and a H$_2$/CO molar feed ratio from 0.3–5.

3. The process of claim 1 wherein said catalyst composition further comprises from about 0.1 t about 10% by weight of manganese, calculated on the basis of the catalyst composition without said manganese.

* * * * *